United States Patent
Steen et al.

(10) Patent No.: US 9,314,225 B2
(45) Date of Patent: Apr. 19, 2016

(54) METHOD AND APPARATUS FOR PERFORMING ULTRASOUND IMAGING

(75) Inventors: Erik Normann Steen, Moss (NO); Menachem Halmann, Wauwatosa, WI (US); Alexander Sokulin, Kiryat Tivon (IL); Arcady Kempinski, Haifa (IL)

(73) Assignee: General Electric Company, Schenectady, NY (US)

( * ) Notice: Subject to any disclaimer, the term of this patent is extended or adjusted under 35 U.S.C. 154(b) by 294 days.

(21) Appl. No.: 13/406,042

(22) Filed: Feb. 27, 2012

(65) Prior Publication Data

US 2013/0226001 A1    Aug. 29, 2013

(51) Int. Cl.
*A61B 8/08* (2006.01)
*A61B 8/00* (2006.01)

(52) U.S. Cl.
CPC ............. *A61B 8/5207* (2013.01); *A61B 8/4427* (2013.01); *A61B 8/4472* (2013.01); *A61B 8/4488* (2013.01); *A61B 8/463* (2013.01); *A61B 8/468* (2013.01); *A61B 8/486* (2013.01); *A61B 8/488* (2013.01); *A61B 8/54* (2013.01); *A61B 8/565* (2013.01)

(58) Field of Classification Search
CPC ... A61B 8/4427; A61B 8/4433; A61B 8/5207
USPC ................................. 600/437, 459
See application file for complete search history.

(56) References Cited

U.S. PATENT DOCUMENTS

| | | | |
|---|---|---|---|
| 5,322,067 A * | 6/1994 | Prater et al. ................ | 600/443 |
| 5,806,521 A * | 9/1998 | Morimoto et al. .......... | 600/447 |
| 6,139,498 A | 10/2000 | Katsman et al. | |
| 6,238,344 B1 * | 5/2001 | Gamelsky et al. .......... | 600/437 |
| 6,475,146 B1 * | 11/2002 | Frelburger et al. ......... | 600/437 |
| 6,491,634 B1 * | 12/2002 | Leavitt et al. .............. | 600/447 |
| 6,526,163 B1 | 2/2003 | Halmann et al. | |
| 7,338,450 B2 | 3/2008 | Kristoffersen | |
| 7,775,982 B2 | 8/2010 | Hazard et al. | |
| 8,012,090 B2 | 9/2011 | Steen | |
| 2002/0165453 A1 * | 11/2002 | Bae et al. .................... | 600/437 |
| 2008/0208061 A1 | 8/2008 | Halmann | |
| 2009/0131793 A1 | 5/2009 | Stonefield et al. | |
| 2010/0217123 A1 * | 8/2010 | Eran et al. ................... | 600/437 |
| 2012/0010508 A1 * | 1/2012 | Sokulin et al. ............. | 600/443 |

* cited by examiner

*Primary Examiner* — Peter Luong
(74) *Attorney, Agent, or Firm* — Dean D. Small; The Small Patent Law Group, LLC

(57) ABSTRACT

An ultrasound system includes an ultrasound probe having a transducer array for acquiring ultrasound data and a first beamformer for partially beamforming the information received from the transducer array, and a portable host system in communication with the ultrasound probe, the portable host system including a second beamformer to perform additional beamforming on the partially beamformed data received from the ultrasound probe.

28 Claims, 6 Drawing Sheets

METHOD AND APPARATUS FOR PERFORMING ULTRASOUND IMAGING

BACKGROUND OF THE INVENTION

The subject matter disclosed herein relates generally to ultrasound imaging systems, and more particularly, to a method and apparatus for performing ultrasound imaging.

Ultrasound imaging systems typically include ultrasound scanning devices, such as, ultrasound probes having different transducers that allow for performing various different ultrasound scans (e.g., different imaging of a volume or body). The ultrasound probes are typically physically connected to a operator console that is located in a medical facility, for example, for controlling the operation of the probes. The probes include a scan head having a plurality of transducer elements (e.g., piezoelectric crystals), which may be arranged in an array. The operator console controls a transmitter that drives the transducer elements within the array during operation, such as, during a scan of a volume or body, which may be controlled based upon the type of scan to be performed. The operator console includes a plurality of channels for communicating with the probe, which may transmit pulses for driving the transducer elements and for receiving signals therefrom.

Portable ultrasound systems are used in a variety of imaging system applications. For example, portable ultrasound systems may be utilized to perform various procedures that were once only accomplished in a dedicated medical facility, for example, a hospital. Accordingly, at least one known portable ultrasound system includes an ultrasound probe that acquires the ultrasound information and a portable operator console that processes the ultrasound information to generate an image. More specifically, in operation the conventional ultrasound probe transmits analog information acquired from the transducers to the operator console. The known operator console includes hardware to process the analog information and to generate an image. For example, at least one known portable operator console includes a plurality of analog-to-digital (A/D) converters that convert the acquired analog information to digital information. The known operator console then utilizes the digital information to generate the image. Accordingly, known portable ultrasound systems are similar to non-portable ultrasound systems, but are fabricated as smaller devices to enable a user to carry the portable ultrasound system.

However, while conventional portable ultrasound systems provide beneficial scans at remote locations, users are still required to carry the portable ultrasound system to the various remote locations.

BRIEF DESCRIPTION OF THE INVENTION

In one embodiment, an ultrasound imaging system is provided. The ultrasound system includes an ultrasound probe having a transducer array for acquiring ultrasound data and a first beamformer for partially beamforming the information received from the transducer array, and a portable host system in communication with the ultrasound probe, the portable host system including a second beamformer to perform additional beamforming on the partially beamformed data received from the ultrasound probe.

In another embodiment, an ultrasound probe is provided. The ultrasound probe includes a transducer array for acquiring ultrasound data, a beamformer for partially beamforming the information received from the transducer array, and a transceiver for transmitting the partially beamformed information to a portable host system.

In a further embodiment, a method of operating an ultrasound imaging system is provided. The method includes receiving analog ultrasound data from a transducer array installed in an ultrasound probe, partially beamforming the ultrasound data to generate partially beamformed ultrasound data, converting the partially beamformed ultrasound data to digital ultrasound data, transmitting the digital ultrasound data from the ultrasound probe to a portable host system, and performing additional beamforming on the digital ultrasound data using the portable host system.

DETAILED DESCRIPTION OF THE INVENTION

Figure 1:
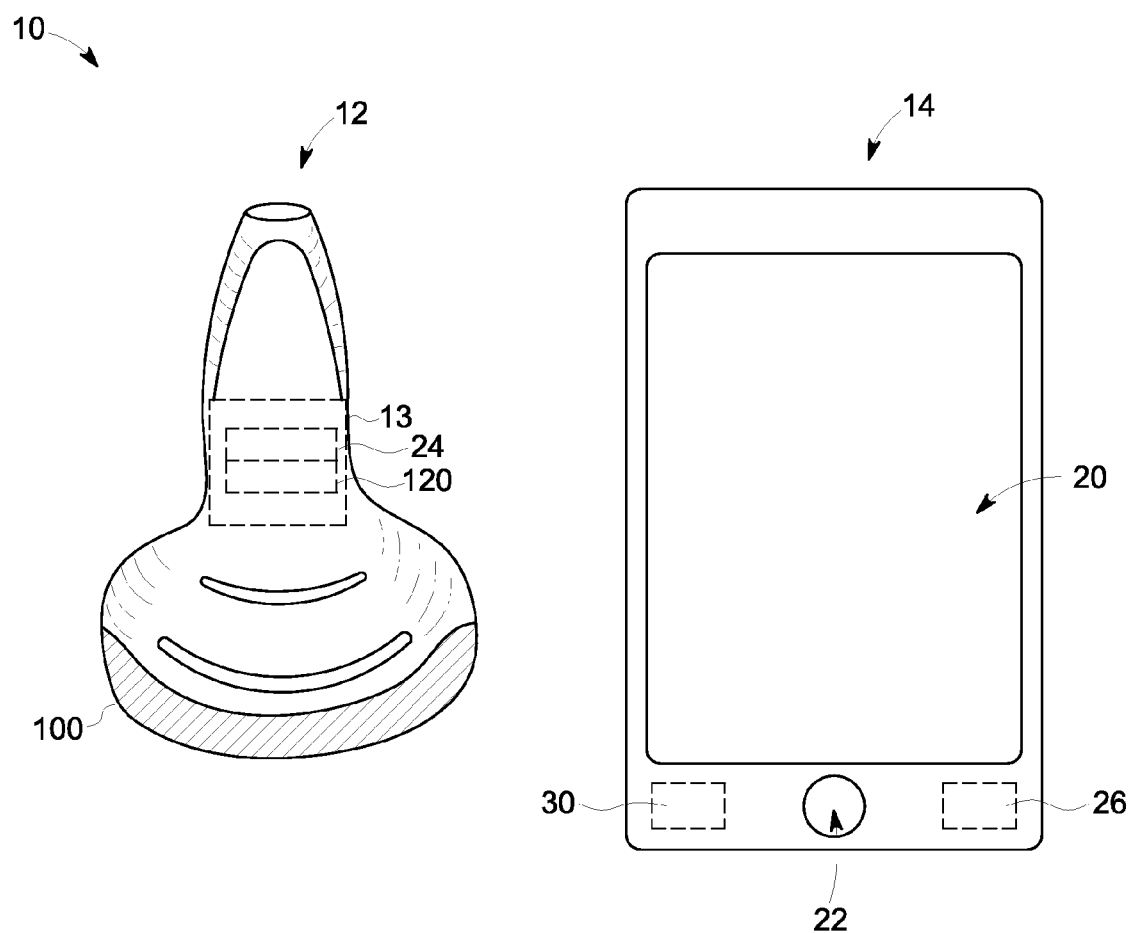
FIG. 1 illustrates an exemplary imaging system formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "generating an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

Described herein are various embodiments for a portable ultrasound imaging system. The portable ultrasound imaging system includes an ultrasound probe and a portable host system that is configured to receive information from the ultrasound probe. The ultrasound probe is configured to convert analog information to digital information. The portable host system includes components that are configured to utilize the digital information to generate an ultrasound image of an object of interest.

Accordingly, in various embodiments, a user may utilize a mobile device, such as a smart phone, to perform ultrasound examinations by connecting the device to an ultrasound probe. Moreover, software running on the mobile device may be programmed to automatically adjust the performance level to the capabilities of the mobile device. Additionally, the manufacturer of ultrasound systems may introduce new and improved signal processing and image processing algorithms as new and more powerful mobile devices enter the market, without having to develop any additional hardware.

Various embodiments described herein may be implemented as an ultrasound imaging system 10 as shown in FIG. 1. More specifically, FIG. 1 illustrates an exemplary ultrasound imaging system 10 that is constructed in accordance with various embodiments. The ultrasound imaging system 10 includes an ultrasound probe 12 and a portable host system 14, which in various embodiments, may be a portable computer 14.

Figure 2:
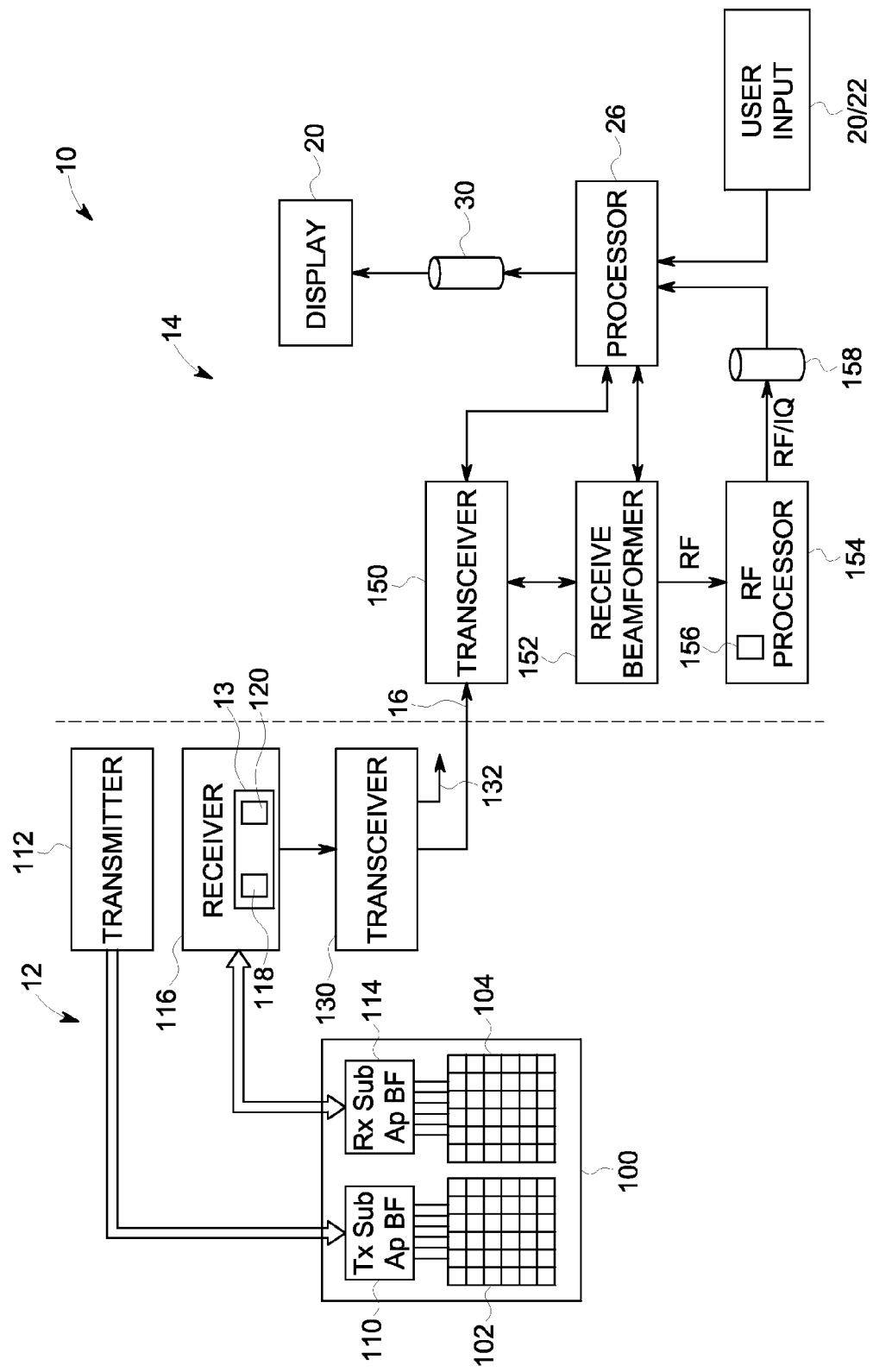
FIG. 2 is a block diagram of the imaging system shown in FIG. 1.

The ultrasound probe 12 includes a transducer array 100, such as a phased array having electronics to perform sub-aperture (SAP) beamforming. In various embodiments, the ultrasound probe 12 may also include an analog front end (AFE) 13 having integrated A/D converters 120, which are shown in FIG. 2, installed therein, as well as an interface for transfer of digital data to the host system 14. The ultrasound probe 12 may be connected wirelessly or with a cable to the host system 14. In one embodiment, the ultrasound probe 14 may be a universal probe which integrates both a phased array transducer and a linear transducer into the same probe housing.

The host system 14 is a portable hand-held device that may be embodied as, for example, a smart phone. The term "smart phone" as used herein, means a portable device that is operable as a mobile phone and includes a computing platform that is configured to support the operation of the mobile phone, a personal digital assistant (PDA), and various other applications. Such other applications may include, for example, a media player, a camera, a global positioning system (GPS), a touchscreen, an internet browser, Wi-Fi, etc. The computing platform or operating system may be, for example, Google Android™, Apple iOS, Microsoft Windows™, Blackberry, Linux, etc. Moreover, the host system 14 may also be embodied as an electronic tablet, such as for example, a Kindle™ or iPad™. The host system 14 may include a touchscreen 20 that functions as a user input device and a display, another user input device such as, for example, a thumbwheel 22, and a memory 30.

In various embodiments, the ultrasound probe 12 includes the AFE which may include built-in electronics 24 that enable the ultrasound probe 12 to transmit digital signals to the host system 14. The host system 14 then utilizes the digital signals to reconstruct an image based on the information received from the ultrasound probe 12. The host system 14 includes a processor 26 that is configured to execute software algorithms for beamforming as well as subsequent signal and image processing steps utilized to process and display the ultrasound information received from the ultrasound probe 12. In various embodiments, the host system 14 includes hardware components, including the processor, that are installed on a single "System-On-Chip" (SOC) device. The SOC device may include multiple CPU cores and at least one GPU core. In operation, the algorithms installed on the processor are dynamically configured according to a probe/application as well as the computing and/or power supply capabilities of the host system 14.

FIG. 2 is a block diagram of the imaging system 10 shown in FIG. 1. In various embodiments, the ultrasound probe 12 includes a two-dimensional (2D) array 100 of elements. The ultrasound probe 12 may also be embodied as a 1.25 D array, a 1.5 D array, a 1.75 D array, a 2D array, and the like. Optionally, the ultrasound probe 12 may be a stand-alone continuous wave (CW) probe with a single transmit element and a single receive element. In various embodiments, the ultrasound probe includes a transmit group of elements 102 and a receive group of elements 104. A sub-aperture transmit beamformer 110 controls a transmitter 112 which, through transmit sub-aperture beamformers 110, drives the group of transmit elements 102 to emit, for example, CW ultrasonic transmit signals into a region of interest (e.g., human, animal, underground cavity, physical structure and the like). The transmitted CW ultrasonic signals are back-scattered from structures in the object of interest, like blood cells, to produce echoes which return to the receive group of elements 104. The receive group of elements 104 convert the received echoes into analog signals as described in more detail below. A sub-aperture receive beamformer 114 partially beamforms the signals received from the receive group of elements 104 and then passes the partially beamformed signals to a receiver 116.

More specifically, the sub-aperture transmit beamformer 110 is configured to reduce the number of system channels utilized to process signals from the large number of transducer elements 102. For example, assume that there are m elements 102. In various embodiments, m channels are then utilized to couple the m elements 102 to the sub-aperture beamformer 110. The sub-aperture beamformer 110 then functions such that n channels of information are passed between the transmitter 112 and the sub-aperture beamformer 110, wherein n<m. Moreover, assume that there are m elements 104. In various embodiments, m channels are then utilized to couple the m elements 104 to the sub-aperture beamformer 114. The sub-aperture beamformer 114 then functions such that n channels of information are passed between the receiver 116 and the sub-aperture beamformer 114, wherein n<m. Thus, the sub-aperture beamformers 110 and 114 function to output fewer channels of information than are received from the elements 102 and 104.

In various embodiments, the receiver 116 may include the AFE 13. The AFE 13 may include for example, a plurality of demodulators 118 and a plurality of analog/digital (A/D) converters 120. In operation, the complex demodulators 118 demodulate the RF signal to form IQ data pairs representative of the echo signals. The I and Q values of the beams represent in-phase and quadrature components of a magnitude of echo signals. More specifically, the complex demodulators 118 perform digital demodulation, and optionally filtering as described in more detail herein. The demodulated (or downsampled) ultrasound data may then be converted to digital data using the A/D converters 120. The A/D converters 120 convert the analog outputs from the complex demodulators 118 to digital signals that are then transmitted to the host system 14 via a transceiver 130. In various embodiments, the transceiver 130 is configured to wirelessly transmit and/or receive digital information from the host system 14. In other embodiments, the ultrasound probe 12 may be physically coupled to the host system 14 via a cable 132.

In various embodiments, the host system 14 includes a transceiver 150 that is configured to wirelessly transmit and/or receive digital information to/from the ultrasound probe 12. In the exemplary embodiment, the beamformers 110 and 14, and the complex demodulators 118 facilitate reducing the quantity of information that is transmitted from the ultrasound probe 12 to the host system 14. Accordingly, the quantity of information being processed by the host system 14 is reduced and ultrasound images of the patient may be generated, by the host system 14, in real-time as the information is being acquired from the ultrasound probe 12. In the exemplary embodiment, the digital ultrasound information received from the ultrasound probe 12 may be transmitted directly to a receive beamformer 152. Optionally, the digital ultrasound information received from the ultrasound probe 12 may be transmitted directly to the processor 26. The processor 26 may then be configured to transmit at least a portion of the digital information to the beamformer 152 for additional processing.

In various embodiments, the beamformer 152 receives the ultrasound information and performs the additional or final beamforming. More specifically, as discussed above, the demodulators 118 reduce the quantity of channels of information from m channels to n channels. In operation, the beamformer 152 is configured to reduce the n channels to a single RF signal. The RF signal output from the beamformer 152 is transmitted to an RF processor 154.

In various embodiments, the RF processor 154 may include a complex demodulator 156 that demodulates the RF signal to form IQ data pairs representative of the echo signals. More specifically, in various embodiments, the probe 12 does not include the demodulators 118, rather demodulation is performed by the complex demodulator 156 within the host system 14. More specifically, the complex demodulator 156 performs digital demodulation, and optionally filtering as described in more detail herein. The demodulated (or downsampled) ultrasound data may be stored in a memory 158, such as temporarily to perform one or more embodiments described herein. The complex demodulator 156 demodulates the RF signal to form IQ data pairs representative of the echo signals, which in various embodiments have a reduced data transfer rate than the transfer rate of the ADC 120. Optionally, the complex demodulator 156 may be omitted or replaced by some other signal processing algorithm. The RF or IQ element data may then be routed directly to the memory 158 for storage.

The processor 26 further processes the output of the RF processor 154 and prepares frames of ultrasound information for display on the display 20. In operation, the processor 26 is adapted to perform one or more processing operations according to a plurality of selectable ultrasound modalities on the acquired ultrasound data. The processor 26 is connected to the user interface 20/22 (which may include a mouse, keyboard, touch panel, etc.) that may control operation of the processor 26 as explained below in more detail. The display 20 includes one or more monitors that present patient information, including diagnostic ultrasound images to the user for diagnosis and analysis, as well as monitoring information as described herein. Images displayed on the display 20 may be modified and the display settings of the display 20 may also be manually adjusted using the user interface 20/22.

The beamformer 152 and the RF processor 154 may be software running on the processor 26 or hardware provided as part of the processor 26. It should be noted that although the various embodiments may be described in connection with a medical ultrasound system, the methods and systems are not limited to medical ultrasound imaging or a particular configuration thereof. The various embodiments may be implemented in non-medical imaging systems, for example, non-destructive testing systems such as ultrasound weld testing systems or airport baggage scanning systems.

Figure 3:
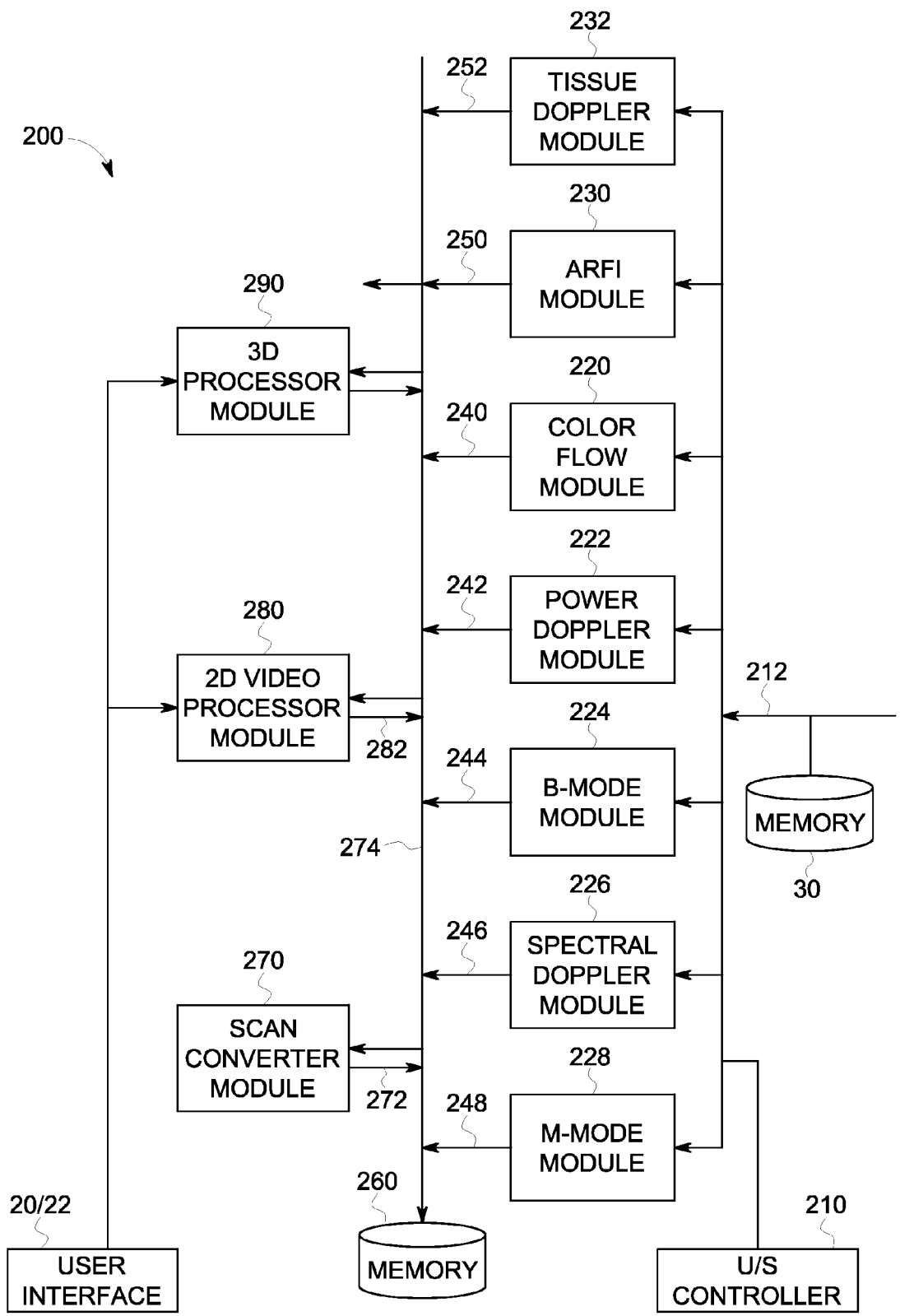
FIG. 3 is a block diagram of an ultrasound processor module of the ultrasound imaging system of FIG. 1 formed in accordance with various embodiments.

FIG. 3 illustrates an exemplary block diagram of an ultrasound processor module 200, which may be embodied as the processor 26 of FIG. 2 or a portion thereof. The ultrasound processor module 200 is illustrated conceptually as a collection of sub-modules, but may be implemented utilizing any combination of dedicated hardware boards, DSPs, processors, etc. Alternatively, the sub-modules of FIG. 3 may be implemented utilizing a single processor or multiple processors, with the functional operations distributed between the processors, for example also including a Graphics Processor Unit (GPU). As a further option, the sub-modules of FIG. 3 may be implemented utilizing a hybrid configuration in which certain modular functions are performed utilizing dedicated hardware, while the remaining modular functions are performed utilizing a processor. The sub-modules also may be implemented as software modules within a processing unit.

The operations of the sub-modules illustrated in FIG. 3 may be controlled by a local ultrasound controller 210 or by the processor module 26. The sub-modules perform midprocessor operations. The processor module 26 may receive ultrasound data 212 in one of several forms. In the exemplary embodiment of FIG. 2, the received ultrasound data 212 constitutes I,Q data pairs representing the real and imaginary components associated with each data sample. The I,Q data pairs are provided to one or more of a color-flow sub-module 220, a power Doppler sub-module 222, a B-mode sub-module 224, a spectral Doppler sub-module 226 and an M-mode sub-module 228. Optionally, other sub-modules may be included such as an Acoustic Radiation Force Impulse (ARFI) sub-module 230 and a Tissue Doppler (TDE) sub-module 232, among others.

Each of sub-modules 220-232 are configured to process the I,Q data pairs in a corresponding manner to generate color-flow data 240, power Doppler data 242, B-mode data 244, spectral Doppler data 246, M-mode data 248, ARFI data 250, and tissue Doppler data 252, all of which may be stored in a memory 260 (or memory 30 shown in FIG. 2) temporarily before subsequent processing. For example, the B-mode sub-module 224 may generate B-mode data 244 including a plurality of B-mode image planes, such as in a biplane or triplane image acquisition as described in more detail herein.

The data 240-252 may be stored in the memory 260, for example, as sets of vector data values, where each set defines an individual ultrasound image frame. The vector data values are generally organized based on the polar coordinate system. Alternately or additionally the data may be stored as beamformed I,Q data in the memory 30 or 158.

A scan converter sub-module 270 accesses and obtains from the memory 260 the vector data values associated with an image frame and converts the set of vector data values to Cartesian coordinates to generate an ultrasound image frames 272 formatted for display. The ultrasound image frames 272 generated by the scan converter module 270 may be provided back to the memory 260 for subsequent processing or may be provided to the memory 30 or 156.

Once the scan converter sub-module 270 generates the ultrasound image frames 272 associated with, for example, B-mode image data, and the like, the image frames 272 may be restored in the memory 260 or communicated over a bus 274 to a database (not shown), the memory 260, the memory 30, the memory 156, and/or to other processors.

The scan converted data may be converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 20 (shown in FIG. 1), which may include one or more monitors or windows of the display, to display the image frame. The image displayed in the display 20 is produced from image frames of data in which each datum indicates the intensity or brightness of a respective pixel in the display.

Referring again to FIG. 3, a 2D video processor sub-module 280 combines one or more of the frames generated from the different types of ultrasound information. For example, the 2D video processor sub-module 280 may combine a different image frames by mapping one type of data to a grey map and mapping the other type of data to a color map for video display. In the final displayed image, color pixel data may be superimposed on the grey scale pixel data to form a single multi-mode image frame 282 (e.g., functional image) that is again re-stored in the memory 260 or communicated over the bus 274. Successive frames of images may be stored as a cine loop in the memory 260 or the memory 30 (shown in FIG. 1). The cine loop represents a first in, first out circular image buffer to capture image data that is displayed to the user. The user may freeze the cine loop by entering a freeze command at the user interface 20 or 22. The user interface 20 or 22 may include, for example, a keyboard and mouse and all other input controls associated with inputting information into the ultrasound system 10 (shown in FIG. 1).

A 3D processor sub-module 290 is also controlled by the user interface 20 or 22 and accesses the memory 260 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

Figure 4:
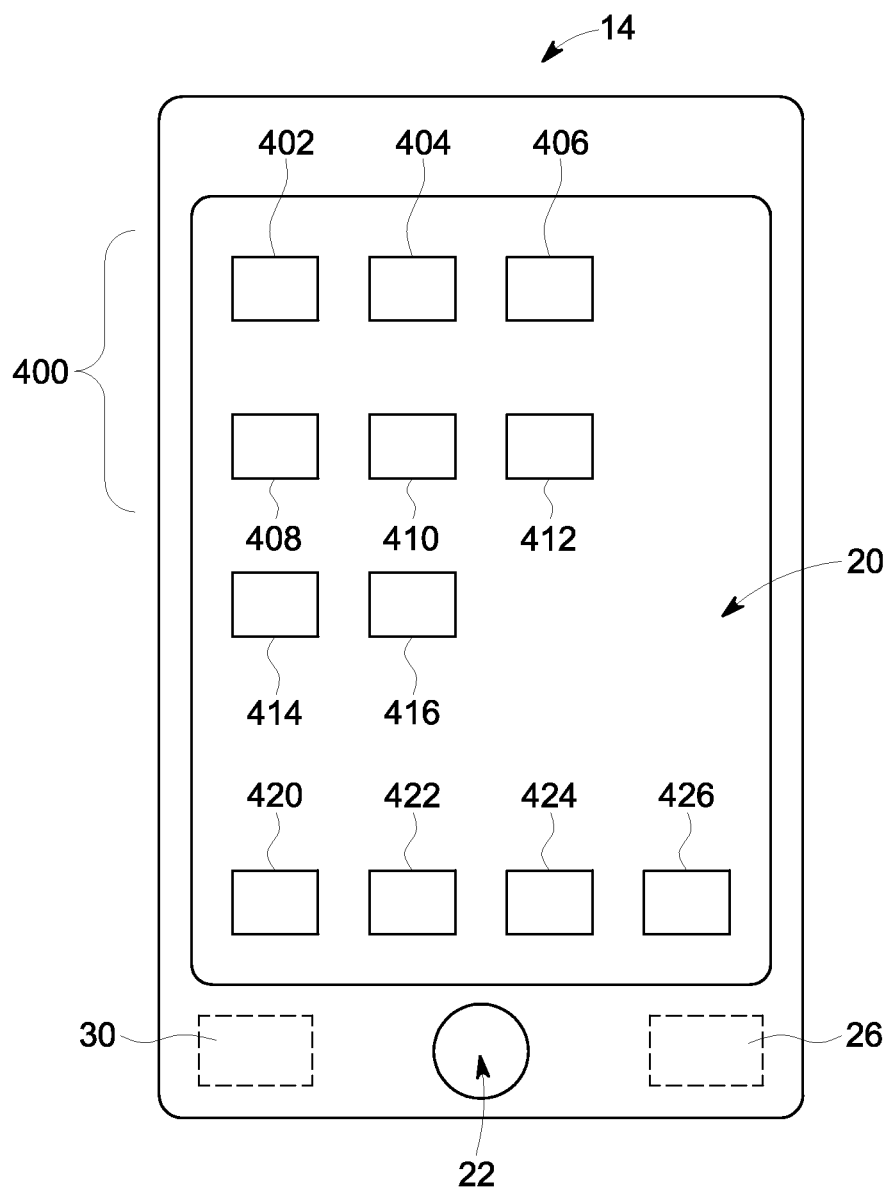
FIG. 4 is a screen shot of a plurality of exemplary icons that may be displayed on the host system shown in FIG. 1 in accordance with various embodiments.

FIG. 4 is a screen shot of a plurality of exemplary icons 400 that may be displayed on the host system 14. It should be noted that the layout of the icons 400 is merely for illustration and different layouts may be provided. In various embodiments, the icons 400 may include, for example, an ultrasound imaging system icon 402, and various other icons. For example, it should be realized that the primary function of the host system 14 is to enable a user to transmit and receive information as a phone or over the internet. Accordingly, the host system 14 enables the user to download and operate a variety of non-medical applications that may be utilized by the host system 14. Therefore, in various embodiments, the host system 14 may also include various other icons 400, such as an Internet access icon 404, a global positioning system icon 406, a weather icon 408, a settings icon 410, a mail icon 412, a photo icon 414 and/or a music icon 416. In operation, the user selects a desired icon 400 to activate the selected function. The icons may be any graphical and/or text based selectable elements. For example, the icon 402 may be shown as an image of an ultrasound probe.

Figure 5:
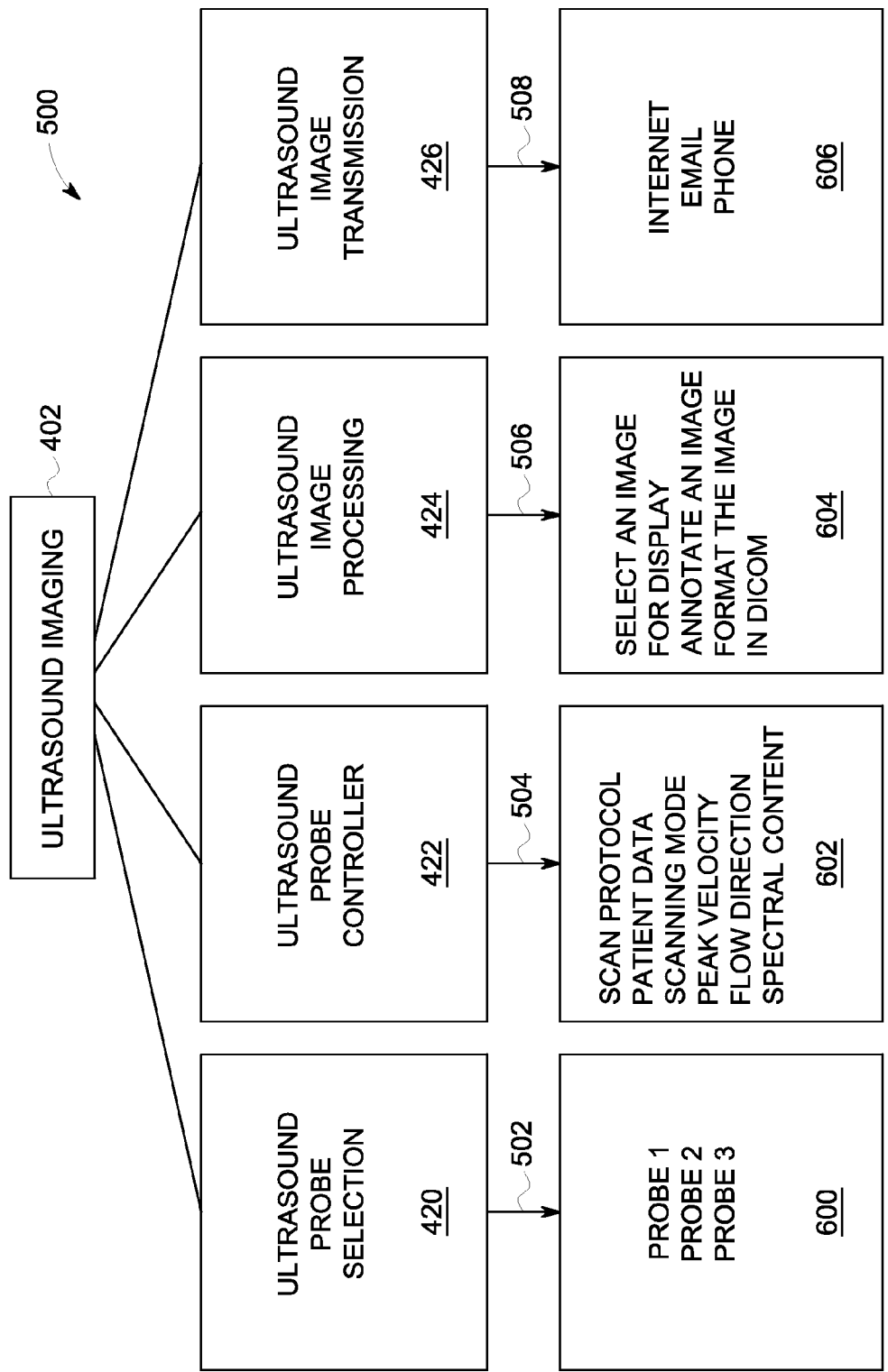
FIG. 5 is a simplified workflow diagram illustrating the operation of the host system shown in FIG. 1 in accordance with various embodiments.

FIG. 5 is a simplified workflow diagram 500 illustrating the operation of the host system 14. In operation, the host system 14 may be operated as an ultrasound imaging system by selecting for example, the ultrasound imaging icon 402. In response to selecting the ultrasound imaging icon 402, the host system 14 may be programmed to display, for example, an ultrasound probe selection icon 420, an ultrasound probe controller icon 422, an ultrasound image processing icon 424, and an ultrasound image transmission icon 426, all shown in FIG. 4.

Once the ultrasound imaging icon 402 is selected, the host system 14 may display various screens or icons to enable the user to identify an ultrasound probe to be utilized to perform ultrasound imaging, such as icons 420, 422, 424, and 426, described above. For example, initially the user may select the icon 402 to select an ultrasound probe to be utilized to perform the ultrasound imaging procedure. FIG. 5 illustrates an exemplary screen 600, having selectable text, that may be displayed when the ultrasound probe selection icon 420 is initially selected at 502. In various embodiments, the host system 14 may generate and transmit a predetermined signal to identify an ultrasound probe. More specifically, the host system 14 may be configured to transmit a signal that is received by various ultrasound probes in the vicinity of the host system 14, such as the ultrasound probe 12 shown in FIG. 1. Optionally, an ultrasound probe, such as probe 12, may transmit a signal that is received by the host system 14.

In various embodiments, the host system 14 is configured to display the ultrasound probes identified by the host system 14. For example, as shown in FIG. 5, the screen 600 indicates that three ultrasound probes are available to perform ultrasound imaging. The operator may then select one of the probes displayed, e.g. by touching a corresponding icon or using a physical button to select the icon. Optionally, the host system 14 may automatically select an appropriate ultrasound probe based on information provided by the user. For example, the user may desire to perform a fetal scan of a patient. Thus, the host system may automatically select a surface probe to perform the fetal scan.

At 504, and in response to the selection of the desire ultrasound probe, the host system 14 may automatically display a screen, such as the ultrasound probe controller screen 602, having selectable text, to enable the user to input various scan parameters to control the operation of the selected ultrasound probe. Optionally, after the probe has been selected, the host system 14 may display the ultrasound icons 420, 422, 424, and 426, and the operator may manually select the ultrasound probe controller icon 422 to activate the screen 620 and enable the operator to manually input information or scan parameters to control the scanning operation of the ultrasound probe. Such scan parameters may include, for example, selecting a scan protocol, controlling the input of patient data, changing a scanning mode, determining peak velocity, flow direction, spectral content of the flow, and the like. The user may then initiate the ultrasound scanning procedure to acquire ultrasound information.

At 506, the host system 14 may automatically display a screen, such as the image processing screen 604, having selectable text, to enable the user to perform ultrasound image processing. Optionally, after the ultrasound imaging procedure is completed, the host system 14 may display the ultrasound icons 420, 422, 424, and 426, and the operator may manually select the image processing icon 424 to activate the image processing screen 604. The user may then enter information on the screen 604 to perform image processing on the acquired ultrasound information. Such image processing may include, for example, instructing the host system 14 to generate a B-mode image, to perform digital demodulation, to perform various filtering operations, to adjust the size, contrast and/or colors of the acquired images, etc.

The image processing screen 604 may also be configured to enable the user to annotate the acquired images. More specifically, the screen 604 may be configured to enable the user to annotate ultrasound images to include textual information that provides descriptive or identifying information of the image. Such textual information may include information that describes the owner or author of the image, a title or label of the image, a sequence number of the image, type of examination, hospital, date of examination, type of acquisition, type of scan, the orientation of the image, the use of special image processing filters, and/or statistics associated with regions of interest shown on the image. The annotations may also include arrows or indicia pointing to a region of interest.

The image processing screen 424 may also be configured to enable the acquired ultrasound information or images to be encoded in a DICOM file format to enable the acquired information to be transmitted and utilized by remote medical facilities.

At 508, the host system 14 may automatically display a screen, such as an ultrasound image transmission screen 606, having selectable text, to enable the user to transmit the ultrasound information, e.g. raw or processed data, or ultrasound images to a remote user. For example, the host system 14 enables the ultrasound information to be transmitted via the Internet to a remote user. The host system 14 enables the ultrasound information to be transmitted via an email to the remote user and/or the user may use the phone interface to verbally contact a remote user to discuss the imaging procedure. Moreover, the host system 14 enables the remote user to transmit ultrasound information to the user of the host system 14. The user may then utilize the host system 14 to process the ultrasound information, generate ultrasound images, annotate the ultrasound images, and retransmit the information to another user via the Internet, email, or phone.

Figure 6:
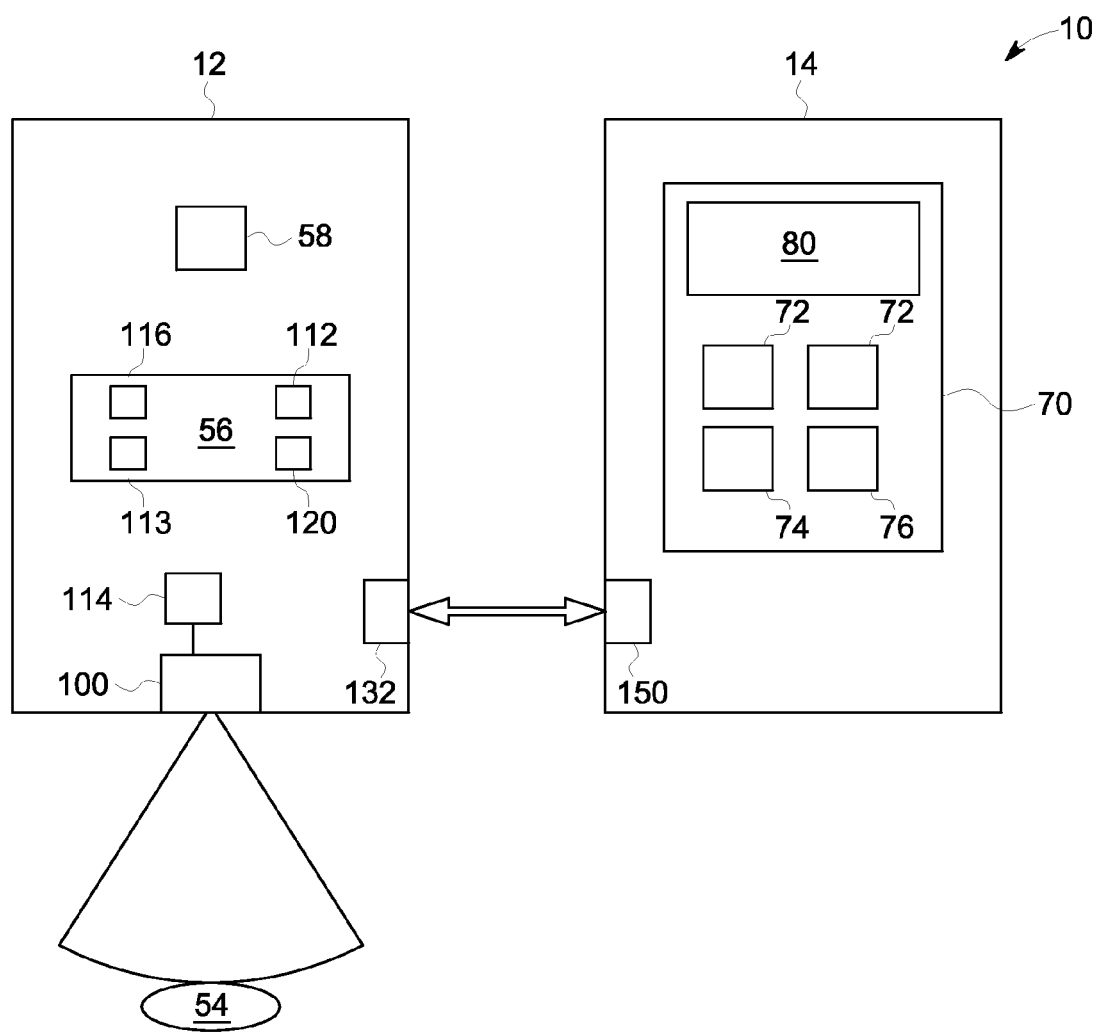
FIG. 6 is a block diagram of one configuration for the imaging system shown in FIG. 1 in accordance with various embodiments.

FIG. 6 is a block diagram of one configuration of the imaging system 10 shown in FIG. 1 in accordance with various embodiments. As described above, the imaging system 10 includes the ultrasound probe 12 that includes the AFE 13. The AFE 13 may be implemented as an ASIC and include, for example, the transmitter 112, the receiver 116, Low Noise Amplifiers (LNAs) 113, the ADCs 120, as well as circuitry for resampling and complex demodulation of the ultrasound signals to facilitate further reducing the sampling rate.

In operation, and as described above, the ultrasound probe 12 utilizes the transducer array 100 to emit, for example, CW ultrasonic transmit signals into a region of interest, such as the object 54. The transmitted CW ultrasonic signals are back-scattered from object 54, to produce echoes which return to the transducer array 100. A sub-aperture receive beamformer 114 then partially beamforms the signals received from the transducer array 100 and then passes the partially beamformed signals to data acquisition circuitry 56, which may include, for example, the transmitter 112 and/or the receiver 116. The integrated A/D converters 120 process the analog information received from the AFE 13 to form digital information that is transmitted, via the transceiver 132, to the host system 14.

The AFEs may be ASICS which include Low Noise Amplifiers (LNAs), ADCs as well as resampling and complex demodulation of the original signal in order to further reduce the sample rate. The ultrasound probe 12 may further include electronics, such as the transceiver 132, for transferring only digital data wirelessly or through a cable to the host system 14 using a transfer protocol supported by the host system 14. In various embodiments, the ultrasound probe 12 may also include a controller unit 58 that is configured to receive control signals from the host system 14 to setup both transmit sequences as well as the AFE 13.

The host system 14, which in various embodiments, is a smart phone, a notepad, or a tablet device, includes a System-on-Chip (SOC) device 70. The SOC 70 in various embodiments, may include, for example, a combination of one or more CPUs or CPU cores 72, one or more GPUs or GPU cores 74 and optionally at least one digital signal processing (DSP) core 76. The SOC 70 may also include a reconfigurable ultrasound control module 80. In operation, the control module 80 processes the data received from the ultrasound probe 12 to generate a digital image that may be displayed on the display of the host system 14. The SOC 70 executes a software program that performs digital beamforming using one or more of the CPU cores 72, the GPU cores 74 and/or the DSP cores 76 or a combination thereof. The SOC 70 may further execute a software program that performs scan conversion. The scan conversion transforms ultrasound information into an ultrasound image that may be displayed on the host system 14. The scan conversion may be executed on one or more of the CPU cores 72, the GPU cores 74, the DSP cores 76, or a combination thereof.

The SOC 70 may also execute additional software programs to provide additional functionality, such as for example, amplitude detection, color flow processing, spatial noise reduction, edge enhancement and temporal noise reduction, among others. In various embodiments, the distribution of different computing tasks between the different cores 72, 74, and 76 may be dynamically changed based on specific application needs. Such applications may include, for example, adaptive beamforming (with phase aberration corrections) and retrospective beamforming algorithms. The various software algorithms may also be configured both according to the performance of the host system 14 and according to the power supply capabilities of the host system 14. For example, quantities of MLAs produced in the software beamforming algorithm may be derived from the supply capabilities of the host system 14. Moreover, the user may be able to control the configuration of the signal chain through a "performance" mode or a "battery saving" mode (e.g. with limited frame rates). The imaging system 10 described herein therefore enables the user to use an existing cell phone, or tablet as an ultrasound scanner. Accordingly, the user does not need to carry a dedicated ultrasound imaging system in addition to the mobile phone or other device. The imaging system 10 described herein also enables the user to purchase an ultrasound probe and a software application with improved performance and image quality using newer generations of tablet/smart phones. Moreover, the software applications may be upgraded over time to reduce an overall cost of operating the imaging system.

Thus, various embodiments provide a mobile ultrasound system 10 that includes an ultrasound probe 12, e.g. a "smart" probe, with built in electronics connected to the host system 14, such as a smart phone, through a standard interface. The mobile ultrasound system 10 includes a system architecture wherein the host system 14 executes software algorithms for beamforming as well as all subsequent signal and image processing for generating and displaying an ultrasound image using a single SOC device 70, which may include multiple CPU cores and at least one GPU core. The algorithms are dynamically configurable according to probe/application as well as the computing and/or power supply capabilities of the mobile device.

The ultrasound probe 12 integrates a transducer array, such as a phased array with electronics for sub-aperture (SAP) beam forming, AFEs 13 (analog front ends with integrated A/D converters) as well as a standard interface for transfer of digital data. The ultrasound probe 12 may be connected wirelessly, or with a cable, to the host system 14, such as the smart phone or the tablet. The ultrasound probe 12 may be a universal probe which integrates both a phased array transducer and a linear transducer into the probe handle.

In one embodiment, the ultrasound probe 12 is configured to perform SAP beamforming to reduce an amount of digital data being transferred to the host system 14 and to also reduce the amount of data being processed by the host system 14. Thus, mobile computers, or host systems, having reduced processing capabilities are still able to perform the image processing methods described herein. The ultrasound probe 12 also includes various electronics for transferring the digital data either wirelessly or through a cable to the host system 14, as described herein which may include using a transfer protocol recognized by the host system 14. USB 3.0 is an example of a digital interface that may be utilized by the imaging system 10. The USB 3.0 standard allows for data transfer speeds up to, for example, 5 GBit/second. After down mixing, the data rate is reduced to cover the bandwidth of the signals from the transducer. The data rate will therefore be substantially higher with a wide band linear transducer compared to a narrow band phased array transducer which is typically used in adult cardiology. With the ultrasound probe 12, which integrates both a linear array and a phased array, the data rate will differ according to which transducer is active: For example, a phased array transducer (for adult cardiac) may have a data rate of 2 MHz*16 channels*16 bits/sample*2 (complex data)=1 GBit/second. A linear array transducer may have a data rate of 6 MHz*12 channels*16 bits/sample*2=2.3 GBit/second. In both cases, the bandwidth is within the USB 3.0 standard (up to 5 GBit/Second). Accordingly, the imaging system 10 may use a standardized digital interface or mobile computing technology. Moreover, the imaging system 10 may provide an increase of image quality over time (by migrating algorithms from mid-range/high end scanners) without having to develop new hardware.

The host system 14 may also be connected to an ultrasound transducer providing 3D ultrasound data. In such cases, the SOC 70 may execute a software program which performs 3D rendering and regular scan conversion. It should be realized that the distribution of different computing tasks between cores of the SOC 70 may be dynamically changed based on specific application needs. For example, one or more GPU cores may be executing a beam forming program while another set of GPU cores may be executing a display or 3D rendering program. The set of processing steps may vary from one application to another. Also, the frame rate may vary according to application (e.g. higher in pediatrics) or even synchronized to the heart rate. Examples of processing steps that may be dynamically configured are adaptive beam forming (with phase aberration corrections) and retrospective beam forming algorithms.

The various software algorithms may be configured both according to the performance of the host system 14 and according to the power supply capabilities of the host system 14. As an example, the number of MLAs produced in the software beam forming algorithm may vary according to the available computational resources in the host system 14 as well as the power supply capabilities of the host system 14. Finally, the user may be able to affect the configuration of the signal chain through a "performance" mode or a "battery saving" mode (e.g. with limited frame rates).

The host system 14 may be programmed, in some embodiments, to configure the processing chain according to which transducer is active, as well as the computational resources available inside the host system 14. For example, the host system 14 may be configured to produce a higher number of receive beams for every transmit beam (MLAs) when the phased array transducer is active and the host system 14 may be configured to produce a substantially lower number of MLAs when the linear array is active. The maximum number of MLAs that may be generated with a given host system 14 may vary depending on which transducer is active because the data rate between various host systems may be different. As another example, a first beam forming algorithm may be used when the phased array transducer is active while another different algorithm is used when the linear array is active. Examples of algorithms are simple beam forming and adaptive beam forming (with phase aberration corrections).

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive, solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An ultrasound system comprising:
   an ultrasound probe having a transducer array for acquiring ultrasound data and a first beamformer for partially beamforming the data received from the transducer array, a plurality of analog-to-digital (A/D) converters configured to convert the partially beamformed data to digital data, and a first digital transceiver to transmit the partially beamformed digital data; and
   a portable host system that constitutes a smartphone or an electronic tablet, the portable host system in communication with the ultrasound probe, the portable host system including a second digital transceiver configured to receive the partially beamformed digital data and at least one programmable device configured to perform non-medical applications and to perform additional beamforming on the partially beam formed digital data in software, wherein the non-medical applications correspond to at least one of an internet browser, a global positioning function, a music function, a weather function, a mail function, or application that transmit or receive information over the internet not based on processing of ultrasound images.

2. The ultrasound system of claim 1, wherein the programmable device activates the non-medical application in response to a user selection on a user interface of a corresponding select non-medical function, and activates a beamforming application in response to a user selection on the user interface of an ultrasound function.

3. The ultrasound system of claim 1, wherein the host system further includes a System-On-Chip (SOC) device, the programmable device being an integral part of the SOC device and further configured to perform the additional beamforming.

4. The ultrasound system of claim 1, wherein the host system further includes a System-On-Chip (SOC) device, the SOC device including at least one Central Processing Unit (CPU) core and at least one graphical processing unit (GPU) core, the host system being configured to distribute a workload between the CPU and the GPU.

5. The ultrasound system of claim 1, wherein the host system further includes a System-On-Chip (SOC) device, the SOC device including at least one CPU core, at least one Digital Signal Processor (DSP) core and at least one GPU core, the host system being configured to distribute a workload between the CPU, DSP and the GPU.

6. The ultrasound system of claim 1, wherein the host system further includes a System-On-Chip (SOC) device, the SOC device being configured to implement at least one of signal amplitude detection and color flow processing.

7. The ultrasound system of claim 1, wherein the host system further includes a System-On-Chip (SOC) device, the SOC device being configured to execute a three-dimensional (3D) rendering algorithm on the ultrasound data.

8. The ultrasound system of claim 1, wherein the host system further includes a System-On-Chip (SOC) device, the SOC device being configured to determine a type of ultrasound probe transmitting the ultrasound data, and process the ultrasound data based on the determined type of ultrasound probe.

9. The ultrasound system of claim 1, wherein the host system further includes a System-On-Chip (SOC) device, the SOC device being configured to implement a phase aberration correction on the ultrasound data.

10. The ultrasound system of claim 1, wherein the host system further includes a System-On-Chip (SOC) device, the SOC device being configured to determine a performance level of the host system and a power capability of the host system, and then to perform ultrasound data processing based on at least one of the performance of the host system and the power capability of the host system.

11. The ultrasound system of claim 1, wherein the ultrasound probe comprises a universal ultrasound probe having at least two probe arrays.

12. The ultrasound system of claim 1, wherein the host system is further configured to dynamically adjust a frame rate of the ultrasound data while acquiring the ultrasound data, the adjustment determined based on computing tasks and at least one of a performance of the host system and a power capability of the host system.

13. The ultrasound system of claim 1, wherein the ultrasound probe is configured to wirelessly transmit only digital signals to the portable host system.

14. The ultrasound system of claim 1, wherein the portable host system is configured to download one or more medical applications.

15. The ultrasound system of claim 1, wherein the non-medical applications includes further includes an application that transmit or receive information as a phone not based on processing of ultrasound images.

16. The ultrasound system of claim 1, wherein the first beamformer is implemented as a hardware device and the second beamformer is implemented in software.

17. The ultrasound system of claim 1, wherein the ultrasound probe further comprises a sub-aperture beamforming module.

18. An ultrasound system comprising:
an ultrasound probe including:
  a transducer array for acquiring ultrasound data;
  a plurality of analog-to-digital (A/D) converters configured to convert analog signals received from the transducer array to digital signals;
  a plurality of complex demodulators configured to generate IQ data pairs that are representative of the digital signals received from the A/D converters;
  a beamformer for partially beamforming the data received from the complex demodulators; and
  a digital transceiver to transmit the partially beam formed digital IQ data to a host system; and
a portable host system that constitutes a smartphone or an electronic tablet, the portable host system is in communication with the ultrasound probe, wherein the portable host includes at least one programmable device configured to perform non-medical applications and to perform additional beamforming on the partially beam formed digital IQ data in software, wherein the non-medical applications correspond to at least one of an internet browser, a global positioning function, a music function, a weather function, a mail function, or application that transmit or receive information over the internet not based on processing of ultrasound images.

19. The ultrasound system of claim 18, wherein the host system is configured to perform a final beam forming of the partially beam formed digital IQ data.

20. The ultrasound system of claim 18, wherein the host system is configured to perform a complex demodulation in software after a final beam forming.

21. The ultrasound system of claim 18, wherein the ultrasound probe is configured to wirelessly transmit only digital signals to the portable host system.

22. The ultrasound system of claim 18, wherein the beamformer is implemented as a hardware device.

23. The ultrasound system of claim 18, further comprising a sub-aperture beamforming module.

24. A method of operating an ultrasound imaging system comprising:
receiving analog ultrasound data from a transducer array installed in an ultrasound probe;
partially beamforming the ultrasound data to generate partially beamformed ultrasound data;
converting the partially beamformed ultrasound data to digital ultrasound data;
transmitting the digital ultrasound data from the ultrasound probe to a portable host system; and
performing additional beamforming on the digital ultrasound data in software using a programmable device within the portable host system, the portable host system constitutes a smartphone or an electronic tablet, wherein the programmable device is further configured to perform non-medical applications, the non-medical applications correspond to at least one of an internet browser, a global positioning function, a music function, a weather function, a mail function, or application that transmit or receive information over the internet not based on processing of ultrasound images.

25. The method of claim 24, wherein for the partially beamforming operation the ultrasound probe further includes a first beamformer to partially beamform the ultrasound data received from the transducer array, the converting operation further includes using a plurality of analog-to-digital (A/D) converters that are configured to convert the partially beamformed ultrasound data to the digital ultrasound data, and for the transmitting operation the ultrasound probe includes a first digital transceiver to transmit the partially beamformed digital ultrasound data to the host system.

26. The method of claim 24, further comprising utilizing a software application installed in the host system to perform scan conversion on the digital ultrasound data.

27. The method of claim 25, wherein for the partially beamforming operation the ultrasound probe includes a first beamformer to partially beamform the ultrasound data received from the transducer array, for the performing additional beamforming operation the host system includes a second beamformer, the first beamformer being implemented as a hardware device and the second beamformer being implemented in software.

28. The method of claim 24, wherein the ultrasound probe further comprises a sub-aperture beamforming module, said method further comprising performing sub-aperture processing on the analog ultrasound information received from the transducer array.

* * * * *